(12) United States Patent
Straub et al.

(10) Patent No.: US 7,087,620 B2
(45) Date of Patent: Aug. 8, 2006

(54) LIQUID PHARMACEUTICAL FORMULATIONS CONTAINING 3,7-DIAZABICYCLO[3,3,1]NONANE COMPOUNDS AND METHODS OF TREATMENT RELATING TO ANTI-ARRHYTHMIC EVENTS

(75) Inventors: Matthias Straub, Barsinghausen (DE); Johannes Wilhelmus Catharine Maria Jansen, Culemborg (NL); Michiel Henricus de Vries, Weesp (NL); Claus Rudolf Steinborn, Seelze (DE); Werner Cautreels, Weesp (NL)

(73) Assignee: Solvay Pharmaceuticals GmbH, Hannover (DE)

( * ) Notice: Subject to any disclaimer, the term of this patent is extended or adjusted under 35 U.S.C. 154(b) by 0 days.

(21) Appl. No.: 10/715,130

(22) Filed: Nov. 18, 2003

(65) Prior Publication Data

US 2004/0152716 A1   Aug. 5, 2004

Related U.S. Application Data (60) Provisional application No. 60/426,795, filed on Nov. 18, 2002.

(51) Int. Cl.
*A61K 31/44* (2006.01)

(52) U.S. Cl. ........................ 514/292; 514/300
(58) Field of Classification Search ................ 514/300, 514/292
See application file for complete search history.

(56) References Cited

U.S. PATENT DOCUMENTS

| | | | | |
|---|---|---|---|---|
| 4,550,112 A | * | 10/1985 | Schoen et al. ............... 514/278 |
| 4,912,113 A | * | 3/1990 | Schon et al. ................. 514/278 |
| 5,164,401 A | | 11/1992 | Burow et al. |
| 5,324,732 A | * | 6/1994 | Schoen et al. ............... 514/278 |
| 5,532,251 A | * | 7/1996 | Schoen et al. ............... 514/300 |
| 5,576,327 A | * | 11/1996 | Schoen et al. ............... 514/300 |
| 6,026,817 A | * | 2/2000 | Clemens ..................... 128/898 |
| 6,602,880 B1 | * | 8/2003 | Schoen et al. ............... 514/278 |
| 6,790,463 B1 | * | 9/2004 | Hofmann et al. ........... 424/613 |

FOREIGN PATENT DOCUMENTS

EP    0103833 B1    8/1989

OTHER PUBLICATIONS

Medline Abstract of Burgrii, et al., Terapevticheskii arkhiv, (1986) 58(6) 62–5.*

Russian Language Article of Burgrii et al., Terapevticheskii arkhiv, (1986) 58(6) 62–5 (not translated).*

Chio et al., Journal of Clinical Pharmacology, (1978 May–Jun.), 18 (5–6), pp. 266–271.*

* cited by examiner

*Primary Examiner*—Raymond J. Henley, III
(74) *Attorney, Agent, or Firm*—Crowell & Moring LLP (57) ABSTRACT

The present invention relates to the use of 3,7-diazabicyclo[3,3,1]nonane compounds, preferably of 9,9-alkylene-3,7-diazabicyclo[3,3,1]nonane compounds, and most preferably to the use of tedisamil, and the physiologically acceptable acid addition salts and/or solvates thereof, in the form of a liquid pharmaceutical preparation for the treatment and/or inhibition of anti-arrhythmic events in human patients, preferably in conversion of recent onset of atrial fibrillation or flutter to normal sinus rhythm in humans. Furthermore, the invention concerns related methods of treatment and pharmaceutical products.

17 Claims, 1 Drawing Sheet

Fig. 1

LIQUID PHARMACEUTICAL FORMULATIONS CONTAINING 3,7-DIAZABICYCLO[3,3,1]NONANE COMPOUNDS AND METHODS OF TREATMENT RELATING TO ANTI-ARRHYTHMIC EVENTS

CROSS-REFERENCE TO RELATED APPLICATIONS

This application claims priority from U.S. Provisional Application No. 60/426,795, filed Nov. 18, 2002, the entire disclosure of which is incorporated herein by reference.

FIELD OF THE INVENTION

The present invention relates to the use of 3,7-diazabicyclo[3,3,1]nonane compounds, preferably of 9,9-alkylene-3,7-diazabicyclo[3,3,1]nonane compounds, and most preferably to the use of tedisamil, and the physiologically acceptable acid addition salts and/or solvates thereof, in the form of a liquid pharmaceutical preparation for the treatment and/or inhibition of anti-arrhythmic events in human patients, preferably in conversion of recent onset of atrial fibrillation (Afib) or flutter to normal sinus rhythm (NSR) in human patients. Furthermore, the invention relates to method of treatments and to pharmaceutical products.

BACKGROUND OF THE INVENTION 9,9-Alkylene-3,7-diazabicyclononane compounds of formula I and their pharmacological activities are known from published European Patent No. EP 103,833 and the corresponding U.S. Pat. No. 4,550,112, and Finnish Patent No. FI 76,338. Compounds of formula I are a sub-group of the 9,9-N,N'-tetra-substituted 3,7-diazabicyclo[3.3.1]nonane compounds described in the aforementioned patent specifications and can be prepared by the methods described therein. The aforementioned patent specifications disclose that the compounds have useful cardio-active properties, particularly oxygen-saving effects and effects on the heart rate and heart rhythm in general, and are distinguished by a high physiological tolerance. Thus, the compounds show a satisfactory anti-arrhythmic action even at low doses. Moreover, the undesired negative effect on the contractile power of the heart is extremely low; i.e. the compounds have a particularly favorable ratio of anti-arrhythmic or the refractory period of the heart prolonging activities, to negative inotropic secondary activities.

Moreover, as described in Burow et al., U.S. Pat. No. 5,164,401, the compounds also have a pronounced diuretic effect with a favorable ratio between sodium and potassium excretion.

Furthermore, special salts of the 3,7-diazabicyclo[3,3,1]-nonane compounds and their manufacture, in particular of 9,9-alkylene-3,7-diazabicyclo[3,3,1]nonane compounds are described in U.S. Pat. No. 5,324,732. Thus, U.S. Pat. No. 5,324,732 describes fumaric acid salts of these compounds containing 1.5 moles of fumaric acid per mole of the compound.

Atrial fibrillation (AFib) is the most common sustained cardiac arrhythmia requiring hospitalization, and affects millions of people worldwide. The prevalence of AFib increases with age and in the presence of structural heart disease, it is also slightly more common in men than women. AFib is associated with significant mortality and morbidity and impacts significantly on quality of life. Restoration of normal sinus rhythm (NSR) in patients with these arrhythmias may improve their hemodynamic condition, relieve symptoms, and probably reduce embolic risk. Although this may be achieved using DC cardioversion, the technique has limitations such as the need for general anesthesia and hospitalization. Accordingly, pharmacological conversion has been proposed as an attractive alternative; a variety of anti-arrhythmic drugs have been tested for this purpose. However, many of these agents have important side effects such as the potential for pro-arrhythmia, impairment of LV function, or extracardiac unwanted effects. Consequently, there is a need to develop new anti-arrhythmic drugs not only with good clinical efficacy but also with a favorable safety profile.

Tedisamil is a novel class III anti-arrhythmic agent that blocks multiple potassium-channels and slows sinus rate. It prolongs both atrial and ventricular action potential duration by blocking the transient outward $I_{to}$, the ATP-dependent $I_{K-ATP}$, and the delayed rectifier potassium currents $I_{Kr}$, $I_{Ks}$, and $I_{Kur}$. Tedisamil prolongs action potential duration more strongly in the atria than the ventricles. Unlike other selective potassium-channel blocking drugs, tedisamil does not exhibit reverse rate-dependent effects on atrial refractoriness, which makes it far less likely to be pro-arrhythmic. Finally, tedisamil also possesses significant anti-anginal and anti-ischemic properties. The present prospective, randomized, controlled trial evaluated the efficacy and safety of tedisamil for rapid conversion of AFib or AFlu.

SUMMARY OF THE INVENTION

It is the object of the invention to provide novel pharmaceutical formulations and novel medical treatments for human patients in need of treatment and/or inhibition of anti-arrhythmic events.

Another object of the invention is to provide new anti-arrhythmic pharmaceutical formulations having an improved effect in human patients in need of treatment and/or inhibition of anti-arrhythmic events. A further objective of the present invention is providing pharmaceutical products related to the objectives mentioned before.

The objects of the invention are achieved by the surprising discovery that the known beneficial pharmacological properties of 3,7-diazabicyclo-[3,3,1]nonane compounds, preferably of 9,9-alkylene-3,7-diazabicyclo[3,3,1]-nonane compounds, and most preferably tedisamil, and of pharmaceutically acceptable acid addition salts and/or solvates and/or prodrugs of said compounds may be further enhanced in the treatment and/or inhibition of anti-arrhythmic events in human patients, preferably in conversion of recent onset of atrial fibrillation (Afib) or flutter to normal sinus rhythm (NSR) in human patients, when being administered as a liquid formulation according to a specific administration route or scheme instead of a completely single and/or continuous administration. According to a further aspects of the invention, the objects are achieved by providing an anti-arrhythmic liquid pharmaceutical formulation comprising an anti-arrhythmic amount effective in human patients of at least one anti-arrhythmic active 3,7-diaza-bicyclo[3,3,1] nonane compound as described in the present invention, method of treatments and pharmaceutical products adapted or suitable for the specific and inventive administration route or scheme.

The subject matter of the invention is therefore a liquid pharmaceutical formulation comprising a therapeutically effective amount of at least one 3,7-diazabicyclo[3,3,1] nonane compound, or a physiologically acceptable acid addition salt and/or solvate and/or prodrug thereof for the treatment and/or inhibition of anti-arrhythmic events in human patients, preferably in conversion of recent onset of atrial fibrillation (Afib) or flutter to normal sinus rhythm (NSR) in human patients, which liquid pharmaceutical formulation preferably is suited for stepwise or for overall non-continuous and/or optionally for only partially continuous administration preferably for two-step administration of two continuous administration phases.

In particular the subject matter of the invention pertains to a liquid pharmaceutical formulation which is, characterized in that the liquid pharmaceutical formulation is suited for infusion, preferably for stepwise infusion administration, optionally each step being a partially continuous infusion administration, preferably for two-step infusion administration of two continuous infusion administration phases.

DETAILED DESCRIPTION OF CERTAIN EMBODIMENTS

The term liquid means any fluid form of the 3,7-diaza-bicyclo[3,3,1]nonane compound, a physiologically acceptable acid addition salt and/or solvate and/or prodrug thereof, suitable for administration to a human patient. Hence, the liquid formulation may be a solution, an emulsion including micro-emulsion and nano-emulsion, or a suspension including micro-suspension and nano-suspension. The terms stepwise and/or overall non-continuous indicate that the liquid formulation according to the invention is not applied in a completely single and/or continuous step or with a completely single and/or continuous administration scheme, but either in one step with at least two phases with distinct administration dosage scheme, or in at least two steps with distinct administration dosage scheme. Each phase or step may be itself either continuous or only partially continuous. Most preferably each phase or step is continuous.

The 3,7-diaza-bicyclo[3,3,1]nonane compounds, its physiologically acceptable acid addition salts and/or solvates and/or prodrugs thereof, which may be used according to the present invention in the pharmaceutical formulations for the treatment and/or inhibition of anti-arrhythmic events in human patients, preferably for conversion of recent onset of atrial fibrillation (Afib) or flutter to normal sinus rhythm (NSR) in human patients, are 3,7-diazabicyclo[3,3,1]nonane compounds corresponding to the Formula I:

wherein
R1 represents an alkyl group containing from 1 to 6 carbon atoms, an alkylene group containing from 3 to 6 carbon atoms having a double bond which is not linked directly to the nitrogen atom, a cycloalkylalkyl group containing from 4 to 9 carbon atoms, or a benzyl group, R2 represents a lower alkyl group, and
R3 represents a lower alkyl group, or
R2 and R3 together form an alkylene chain containing from 3 to 6 carbon atoms, and
R4 represents an alkyl group containing from 1 to 6 carbon atoms, an alkenyl group containing from 3 to 6 carbon atoms having a double bond which is not linked directly to the nitrogen atom, a cycloalkylalkyl group containing from 4 to 9 carbon atoms,
a group corresponding to the Formula a:

wherein
R5 represents hydrogen, halogen, lower alkyl or lower alkoxy, and
Z represents an alkylene chain containing from 1 to 3 carbon atoms or a propenylene chain having a double bond which is conjugated with the phenyl group, or
a group corresponding to the Formula b:

wherein
R6 represents hydrogen, halogen, lower alkyl or lower alkoxy, and
R7 represents hydrogen, halogen, lower alkyl or lower alkoxy,
or a physiologically acceptable acid addition salt and/or solvate thereof.

Particularly suited compounds according to the invention are compounds of Formula I, wherein R1 represents an alkyl group containing from 1 to 6 carbon atoms or a cycloalkylalkyl group containing from 4 to 7 carbon atoms. In further preferred compounds of Formula I, the substituent R4 represents an alkyl group containing from 1 to 6 carbon atoms, a cycloalkylalkyl group containing from 4 to 7 carbon atoms, or a group corresponding to Formula b.

Preferred compounds suitable according to the present invention are compounds of Formula I, wherein R1 represents an alkyl group containing from 3 to 6 carbon atoms or a cycloalkylalkyl group containing from 4 to 7 carbon atoms, and R4 represents an alkyl group containing from 3 to 6 carbon atoms or a cycloalkylalkyl group containing from 4 to 7 carbon atoms. Said 3,7-diazabicyclo-[3,3,1] nonane compound may be a 9,9-alkylene-3,7-diazabicyclo [3.3.1]nonane compound of Formula I wherein R2 and R3 together form an alkylene chain containing from 4 to 5 carbon atoms, and R1 and R4 independently of one another each denote a straight-chain or branched alkyl group of 3-4 carbon atoms or the cyclopropylmethyl group, and physiologically acceptable acid addition salts and/or solvates thereof. Preferred salts for this group of compounds are fumaric acid salts of 9,9-alkylene-3,7-diazabicyclo[3.3.1]

nonane compounds containing 1.5 moles of fumaric acid per mole of compound of Formula I.

Further preferred suitable compounds according to the present invention are compounds selected from the group consisting of N,N'-dicyclopropyl-methyl-9,9-tetramethylen-3,7-diazabicyclo[3,3,1](tedisamil), N-isobutyl-N'-isopropyl-9,9-pentamethylen-3,7-diazabicyclo[3,3,1]nonane, and physiologically acceptable acid addition salts and/or solvates thereof. Preferred salts for this group of compounds are fumaric acid salts of N,N'-dicyclopropylmethyl-9,9-tetramethylene-3,7-diazabicyclo[3,3,1]nonane (tedisamil) or of N-isobutyl-N'-isopropyl-9,9-pentamethylene-3,7-diazabicyclo[3,3,1]nonane containing 1.5 moles of fumaric acid per mole of said 9,9-alkylene-3,7-diazabicyclo[3.3.1]-nonane compound.

Alternatively, as acid addition salts of the 3,7-diazabicyclo[3,3,1]nonane compounds the hydrochloride salts are also very suitable in the context of the present invention.

Particularly preferred 3,7-diazabicyclo[3,3,1]nonane compounds are the 9,9-alkylene-3,7-diazabicyclo[3.3.1]nonane compound tedisamil and the physiologically compatible acid addition salts and/or solvates and/or prodrugs thereof. These are most preferably used as compounds in the liquid pharmaceutical formulations. If a tedisamil acid addition salt is used, it may preferably be used according to the invention in the form of tedisamil hydrochloride or in the form of tedisamil sesquifumarate. Further pharmacologically compatible acid addition salts of tedisamil are known from European Patent No. EP 103,833. Thus, salts with inorganic acids, e.g. sulfuric acid or hydrohalic acids, especially hydrochloric acid; or with organic acids, for instance lower aliphatic monocarboxylic or dicarboxylic acids such as acetic acid, fumaric acid, tartaric acid, lactic acid, maleic acid, citric acid or salicylic acid; or with sulfonic acids, for instance lower alkyl sulfonic acids such as methane sulfonic acid, or benzene sulfonic acids optionally substituted in the benzene ring by halogen or lower alkyl, such as p-toluene sulfonic acid, are suitable as physiologically acceptable acid addition salts of the compounds of Formula I.

Surprisingly, it has been found that the 3,7,9, 9-tetrasubstituted 3,7-diazabicyclo[3,3,1]nonane compounds corresponding to Formula I are distinguished by superior enhanced effects in anti-arrhythmic human patients, in particular in the conversion of recent onset of atrial fibrillation (Afib) or flutter to normal sinus rhythm (NSR) in human patients, in addition to the aforementioned already known general heart-affecting properties, when administered as a liquid pharmaceutical formulation by stepwise, an overall non-continuous and/or optionally by only partially continuous administration, preferably when administered as a two-step administration of two continuous administration phases, scheme according to the present invention as described in more exemplary detail below, in particular when administered as an infusion regimen.

For example, the liquid pharmaceutical formulation according to the present invention may be containing a first therapeutically effective amount of said 3,7-diazabicyclo[3,3,1]nonane compound, a physiologically acceptable acid addition salt and/or solvate and/or prodrug thereof, being sufficient for the treatment and/or inhibition of anti-arrhythmic events in human patients is administered over a first time period of about 10±2 minutes, preferably of about 10±1 minutes, most preferably of about 10±0.5 minutes, and subsequently a second therapeutically effective amount of said 3,7-diazabicyclo[3,3,1]nonane compound, a physiologically acceptable acid addition salt and/or solvate and/or prodrug thereof, being sufficient for continuing the treatment and/or inhibition, is administered over a second time period of about 20±5 minutes, preferably of about 20±3 minutes, most preferably of about 20±1 minutes. The given time periods are the most recommended ones, however the skilled artisan may modify to a certain extend this dosage scheme.

A further embodiment of the invention pertains to a pharmaceutical products. Hence, the invention pertains to a pharmaceutical product and/or package containing as a medicament in a liquid pharmaceutical formulation a therapeutically effective amount of at least one 3,7-diazabicyclo[3,3,1]nonane compound, at least a physiologically acceptable acid addition salt and/or solvate and/or prodrug thereof, as defined above, and a label, leaflet and/or package insert indicating that said 3,7-diazabicyclo[3,3,1]nonane compound may be administered step-wisely, overall non-continuously and/or optionally only partially continuously, preferably for two-step administration of two continuous administration phases. Such a pharmaceutical product and/or package according to the invention may be characterized in that the label, leaflet and/or package insert outlines that the liquid pharmaceutical formulation is suited for infusion, preferably for stepwise infusion administration, optionally each step being a partially continuous infusion administration, preferably for two-step infusion administration of two continuous infusion administration phases. In particular, in this embodiment of the invention the pharmaceutical product and/or package is characterized in that the label, leaflet and/or package insert outlines that the 3,7-diazabicyclo[3,3,1]nonane compound may be administered according to an administration scheme in which a liquid pharmaceutical formulation comprising a first therapeutically effective amount of said 3,7-diazabicyclo[3,3,1]nonane compound, a physiologically acceptable acid addition salt and/or solvate and/or prodrug thereof, being sufficient for the treatment and/or inhibition of anti-arrhythmic events in human patients, is administered over a first time period of about 10±2 minutes, preferably of about 10±1 minutes, most preferably of about 10±0.5 minutes, and a second therapeutically effective amount of said 3,7-diazabicyclo[3,3,1]nonane compound, a physiologically acceptable acid addition salt and/or solvate and/or prodrug thereof, being sufficient for continuing the treatment and/or inhibition, is administered over a second time period of about 20±5 minutes, preferably of about 20±3 minutes, most preferably of about 20±1 minutes. Preferably the pharmaceutical product and/or package according this embodiment of the invention, is containing as a medicament a therapeutically effective amount of at least one 3,7-diazabicyclo[3,3,1]nonane compound, a physiologically acceptable acid addition salt and/or solvate and/or prodrug thereof, as defined above, in the liquid pharmaceutical formulation.

In yet a further embodiment the invention pertains to a method of treatment and/or inhibition. Therefore, the invention comprises a method of treatment and/or inhibition of anti-arrhythmic events in human patients, preferably in conversion of recent onset of atrial fibrillation (Afib) or flutter to normal sinus rhythm (NSR) in human patients, wherein a liquid pharmaceutical formulation comprising a therapeutically effective amount of at least one 3,7-diazabicyclo[3,3,1]nonane compound, or a physiologically acceptable acid addition salt and/or solvate and/or prodrug thereof, is administered to said human patients, by a stepwise, an overall non-continuous and/or optionally an only partially continuous administration route, preferably for two-step administration of two continuous administration phases. In particular, this method of treatment and/or inhibition according to the invention, the liquid pharmaceutical formulation comprising said therapeutically effective amount of a 3,7-diazabicyclo[3,3,1]nonane compound, or a physiologically acceptable acid addition salt and/or solvate and/or prodrug thereof, is administered by infusion administration route, preferably by stepwise infusion administration, optionally each step being a partially continuous infusion administration, preferably for two-step infusion administration of two continuous administration phases. A preferred method of treatment and/or inhibition according to the invention is characterized in that a liquid pharmaceutical formulation comprising a first therapeutically effective amount of said 3,7-diazabicyclo[3,3,1]nonane compound, a physiologically acceptable acid addition salt and/or solvate and/or prodrug thereof, being sufficient for the treatment and/or inhibition of anti-arrhythmic events in human patients, is administered over a first time period of about 10±2 minutes, preferably of about 10±1 minutes, most preferably of about 10±0.5 minutes, and a second therapeutically effective amount of said 3,7-diazabicyclo[3,3,1]nonane compound, a physiologically acceptable acid addition salt and/or solvate and/or prodrug thereof, being sufficient for continuing the treatment and/or inhibition, is administered over a second time period of about 20±5 minutes, preferably of about 20±3 minutes, most preferably of about 20±1 minutes. In this method of treatment and/or inhibition according to the invention, preferably a therapeutically effective amount of at least one 3,7-diazabicyclo[3,3,1]nonane compound, a physiologically acceptable acid addition salt and/or solvate and/or prodrug thereof, as defined above in detail, is administered.

According to a most preferred embodiments of the present invention, the embodiments, e.g. the liquid pharmaceutical compositions, are suited for being administered as a two-step infusion regimen, wherein over a first time period of about 10±2 minutes, preferably of about 10±1 minutes, most preferably of about 10±0.5 minutes, a first therapeutically effective amount of said 3,7-diazabicyclo[3,3,1]nonane compound, a physiologically acceptable acid addition salt and/or solvate and/or prodrug thereof, being sufficient for the treatment and/or inhibition of an anti-arrhythmic event in a patient, and then subsequently for continuing the treatment and/or inhibition, a second therapeutically effective amount of said 3,7-diazabicyclo[3,3,1]nonane compound, a physiologically acceptable acid addition salt and/or solvate and/or prodrug thereof, being sufficient for continuing the treatment and/or inhibition is administered over a second time period of about 20±5 minutes, preferably of about 20±3 minutes, most preferably of about 20±1 minutes. For the given time periods the most recommended dosages for the two steps or phases shall be exemplified in the following in some more detail. However, it is clear that the skilled artisan may modify to a certain extend this dosage scheme, if appropriate. Usually the total amount of the 3,7-diazabicyclo[3,3,1] nonane compound, preferably tedisamil or one of its salts, based on the quantity of the base compound may range from about 0.16 mg/kg to about 0.64 mg/kg. Examples of specific amounts to be administered by the preferred a two step infusion regimen may amount within this range to 0.16 mg/kg, 0.24 mg/kg, 0.32 mg/kg, 0.48 mg/kg or 0.64 mg/kg. About half (e.g. 50±5 % by wt.) of this total amount (100% by wt.) is administered in the first time period of e.g. about 10±2 minutes, and about the second half (e.g. the remaining 50±5 % by wt. up to 100% by wt.) is administered over a second time period of e.g. about 20±5 minutes. In a specific example of this invention 0.32 mg/kg tedisamil base was used, infusing half the dose over 10 minutes and half the dose over 20 minutes.

Generally the present invention is applicable to patients of any age and/or both genders. However, in a specific embodiment the findings of the present invention are particularly suitable also for the treatment and/or inhibition of anti-arrhythmic events in male patients, preferably in conversion of recent onset of atrial fibrillation (Afib) or flutter to normal sinus rhythm (NSR) in male patients. Hence, in this particular aspect the invention also pertains to a method of treatment and/or inhibition of anti-arrhythmic events in male patients, preferably in conversion of recent onset of atrial fibrillation (Afib) or flutter to normal sinus rhythm (NSR) in male patients, wherein a liquid pharmaceutical formulation comprising a therapeutically effective amount of at least one 3,7-diazabicyclo[3,3,1]nonane compound, or a physiologically acceptable acid addition salt and/or solvate and/or prodrug thereof, is administered to said male patients, by a stepwise, an overall non-continuous and/or optionally an only partially continuous administration route, but most preferably when administered as a two-step administration of two continuous administration phases. In this context the invention also comprises liquid pharmaceutical formulations, which are suited for stepwise, for overall non-continuous and/or optionally for only partially continuous administration, but most preferably suited for administration as a two-step administration of two continuous administration phases of the 3,7-diazabicyclo[3,3,1]nonane compounds, e.g. preferably of tedisamil and its acid addition salts, to a male patient. A further aspect of this embodiment of the invention related to the treating of male patients is directed to a pharmaceutical product and/or package containing as a medicament in a liquid pharmaceutical formulation a therapeutically effective amount of at least one 3,7-diazabicyclo[3,3,1]nonane compound, at least a physiologically acceptable acid addition salt and/or solvate and/or prodrug thereof, as defined further above according to the invention, and a label, leaflet and/or package insert indicating that said 3,7-diazabicyclo[3,3,1]nonane compound may be administered step-wisely, overall non-continuously and/or optionally only partially continuously, most preferably as a two-step administration of two continuous administration phases, to a male patient. The details described in the context of the above general embodiments of invention fully apply also to this particular embodiment related to the treatment and/or inhibition of anti-arrhythmic events in male patients.

The superior anti-arrhythmic effect of the compounds of Formula I in human patients, can be demonstrated by PK/PD modelling and is confirmed by clinical study data which prove the surprising enhanced suitability and efficacy of 3,7-diazabicyclo[3,3,1]nonane compounds, e.g. of tedisamil and its acid addition salts, for the treatment and/or inhibition of anti-arrhythmic effects in human patients, preferably for conversion of recent onset of atrial fibrillation (Afib) or flutter to normal sinus rhythm (NSR) in human patients, when administered as a liquid pharmaceutical formulation by stepwise, an overall non-continuous and/or optionally by only partially continuous administration scheme according to the present invention.

Description of Clinical Study Design and Results
Development of a two step infusion regimen for rapid conversion of recent onset atrial fibrillation/flutter to normal sinus rhythm using PK/PD modeling.

Background: Tedisamil (TEDI) is a new class III anti-arrhythmic agent, blocking various potassium outward currents such as IKur, Ito, IKr, IKs, and IKATP, under development for the rapid conversion of recent onset atrial fibrillation (AF) and flutter (AFL) into normal sinus rhythm (NSR). Intravenous doses of up to 0.24 mg/kg TEDI base, infused over 10 minutes, did not produce any conversions in AF/AFL patients. A two step infusion regimen was developed using a PK/PD model to enhance drug concentration/exposure at the effect site. The PK/PD model was based on the data from a single infusion study. A three-compartment infusion PK model and an effect compartment model with linear link gave the best fit. The model for the PD effect was a simple linear model. The modeling results were validated in a double-blind, placebo-controlled, randomized, two period cross-over study in 18 healthy male subjects, in which a two step infusion regimen of 0.32 mg/kg TEDI base was used, infusing half the dose over 10 minutes and half the dose over 20 minutes.

Aim: The objectives of the study were to assess safety and tolerability and the correlation between TEDI plasma concentrations and QT, QTc, and heart rate, and compare these results with the simulation data.

Methods and Results: TEDI was safe and well tolerated. The expected PD action, i.e. a prolongation of QT and QTc intervals and a distinct decrease in heart rate, was observed over two hours. The PK and PD results were in close agreement with the simulations based on the single infusion PK/PD model: the simulation based on single infusion estimates lied within the 95% confidence interval around the predicted population mean of the study.

Conclusion: The two step infusion regimen is of benefit in the administration of 3,7-diazabicyclo[3,3,1]nonane compounds, e.g. of tedisamil and its acid addition salts, for the treatment and/or inhibition of anti-arrhythmic effects, preferably for conversion of recent onset of atrial fibrillation (Afib) or flutter to normal sinus rhythm (NSR), when administered as a liquid pharmaceutical formulation by stepwise, an overall non-continuous and/or optionally by only partially continuous administration scheme, thereby increasing the time of exposure at the physiologically effect site.

The following excerpt of a clinical study report gives further details of the exemplified two-step infusion procedure.

A double-blind, placebo-controlled, randomized, single iv dose, two periods cross-over study to assess the safety, tolerability, pharmacodynamics and pharmacokinetics during and following a two step infusion of Tedisamil in healthy male subjects was performed with the following drug and dosages: Tedisamil dihydrochloride/0.4 mg/kg body weight infused over 30 minutes.

Objectives:
1. To assess safety and tolerability of tedisamil in healthy male subjects during and following a two step infusion scheme (0.4 mg/kg body weight infused over 30 minutes, with half of the dose infused over 10 minutes and half of the dose infused over the remaining 20 minutes).
2. To examine the correlation between plasma concentrations of tedisamil and the pharmacodynamic variables QT, QTc, and heart rate, calculated from the RR-interval, using the PK/PD model and to compare these results with results gained from a previous simulation study.

Methodology:
This was a single center, double-blind, placebo-controlled, randomized, single iv dose, two period cross-over study. Subjects were randomly allocated to either treatment sequence tedisamil-placebo or placebo-tedisamil. Number of patients (planned, screened, randomized and analyzed): Planned: 18, Screened: 27, Randomized: 18, Analyzed: 18 in PK/PD and safety analyses.

Diagnosis and Main Criteria for Inclusion:
Subjects were included in the study only if they were healthy males, their age was in the range of 18–40 years (both inclusive), their body mass index (BMI) was between 18 kg/m$^2$ and 28 kg/m$^2$. Test product, dose and mode of administration: Tedisamil dihydrochloride; Strength: 2 mg/ml; Dose: 0.4 mg/kg body weight infused over 30 minutes, with half of the dose infused over 10 minutes and half of the dose infused over the remaining 20 minutes. Route: intravenous.

Duration of Treatment
One day per period, at which an infusion over a total duration of 30 minutes was administered. Both drug administrations were separated by a wash-out period of one week.

Criteria for Evaluation:
Efficacy/Pharmacodynamics:
12-lead ECG.s were taken at several time points to explore the pharmacodynamic effects of Tedisamil (effects on QT and QTc) during and following infusion. The maximum value and maximum increase were derived for QTc and QT and the minimum value and maximum decrease were derived for heart rate. The AUC(0-24) and the maximum for the placebo-corrected QTc and QT and the AUC (0-24) and the minimum for the placebo-corrected heart rate were also calculated.

Safety:
Screening assessments included physical examination, ECG, HIV/Hepatitis screening, blood pressure and heart rate measurements, clinical laboratory determinations, urine drug screen, alcohol breath test, and medical history. Follow-up assessments included physical examination, ECG, blood pressure and heart rate measurements, clinical laboratory determinations, and questions for adverse events and concomitant medication. During concomitant administration of Tedisamil, blood pressure, heart rate, and ECGs were recorded. Adverse events and concomitant medication were monitored throughout the study.

Pharmacokinetics:
Blood samples for determination of Tedisamil plasma concentration were taken at several time points during and following intravenous drug administration in both study periods. The following pharmacokinetic parameters were determined: AUC(0-inf), AUC(0-t), $C_{max}$, Tmax, $t_{1/2}$, $\lambda_z$, $V_{ss}$, CL, MRT and the number of data points considered for the determination of terminal half life.

Statistical Methods:
Pharmacodynamics:
Data of subjects who completed both study periods were considered valid for pharmacodynamic/pharmacokinetic analysis.

Descriptive statistics were performed for the ECG intervals QT, QTc, RR, PR, QRS and for heart rate by treatment (tedisamil, placebo and "tedisamil–placebo") and time point. Individual and mean (arithmetic mean±1 SD) time profiles for ECG intervals and heart rate were graphically presented for both treatments.

Derived parameters, i.e. maximum value and maximum increase for QTc and QT, and minimum value and maximum decrease for heart rate were submitted to separate analyses of (co)variance (covariance only for maximum and minimum values) including subject, treatment, sequence, and period as class effects (and the individual pre-dose value as covariate). Point estimates and 95% confidence intervals were constructed for the difference "tedisamil–placebo" using the residual variance. Model assumptions were checked by visual inspection of residual plots. Additionally, descriptive statistics were calculated for the derived parameters per treatment and for the difference "tedisamil–placebo".

Descriptive statistics for the placebo corrected AUC(0-24) of QTc, QT and heart rate and the placebo corrected maximum effect (maximum for QTc and QT and minimum for heart rate) were calculated. In addition, 95% confidence intervals were derived based on normally distributed outcomes.

Safety:

Subjects who received study medication, were considered valid for safety evaluation.

Treatment emergent adverse events, defined as any adverse event present at baseline that worsened or any event that began after treatment with study medication, were summarized by COSTART term for each treatment group. Each adverse event was evaluated for frequency of occurrence, duration, intensity, action taken, outcome, and relationship to administration of the study medication. Adverse events were listed for each subject.

Listings of abnormal or out of range values for each subject were presented for vital signs, laboratory assays, and physical examinations. Adverse events, blood pressure, heart rate and clinical laboratory data were analyzed descriptively and reviewed to evaluate the safety of all randomized subjects. Any clinical abnormalities were described.

Pharmacokinetics:

Geometric means and corresponding 90% confidence intervals were calculated for the plasma concentration of tedisamil at each time-point, for AUC, AUC(0-t), CL, and $C_{max}$.

Arithmetic means and corresponding 90% confidence intervals were calculated for the other variables ($V_{ss}$, $\lambda_z$, $t_{1/2}$, MRT). $T_{max}$ was described using minimum, median, maximum, and frequency counts. Individual and mean plasma-concentration versus time curves were plotted using both linear and semi-logarithmic scale.

Individual and mean plasma-concentration versus time curves were plotted using both linear and semi-logarithmic scale.

Pharmacodynamics/Pharmacokinetics:

Non-linear mixed effect models were used to characterize the pharmacokinetics and pharmacodynamics of tedisamil after two-step infusion. Population mean prediction profiles and confidence limits over time were obtained from the predicted PK and PD profiles generated for each subject.

The pharmacokinetic and pharmacodynamic model of tedisamil infusion established in an earlier single infusion study was validated in three stages:
  i) the best fitting PK model on the single infusion study data-set was determined;
  ii) a joint PK/PD analysis was carried out on the data-set augmented by the data of the single infusion study.
  iii) the population mean PK/PD prediction profiles based on simulations were compared with those based on the single infusion study.

Outlier checks were carried out by global residual plots and plots of observed versus expected.

PK/PD Compartment Models:

The PK model for plasma concentration, Cp, was a three compartmental constant infusion model. To model observed PD effects on ECG parameters, a sequential PK/PD effect-compartment linear link model was used.

Population Analyses:

NONMEM V was used for all pharmacokinetic modeling. The PK/PD linear-link model was fitted using the SAS macro NLINMIX for non-linear mixed modeling.

Summary and Conclusions

Efficacy Results:

Pharmacodynamics:

Descriptive statistics for derived parameters of QT, QTc interval and heart rate are summarized in the Table A below.

TABLE A

Descriptive statistics for derived parameters

| Parameter | Derived Parameter | Tedisamil Arith. Mean (SD) | Placebo Arith. Mean (SD) |
|---|---|---|---|
| QT Interval (ms) | Maximum | 474.2 (39.2) | 416.9 (19.4) |
|  | Max. Increase | 76.0 (22.4) | 18.0 (11.5) |
| QTc Interval (ms) | Maximum | 455.9 (30.0) | 421.9 (21.5) |
|  | Max. Increase | 61.1 (30.3) | 27.0 (13.9) |
| Heart Rate (bpm) | Minimum | 49.2 (7.0) | 52.7 (4.8) |
|  | Max. Decrease | 10.6 (3.8) | 6.4 (3.4) |

Summary of Analyses for the derived parameters of QT, QTc interval and heart rate for the comparison of tedisamil–placebo are given in the table below.

TABLE B

Summary of Analyses for derived parameters

| Parameter | Derived Parameter | Estimate (Ted-Pla) | 95% C. I. lower | 95% C. I. upper |
|---|---|---|---|---|
| QT Interval (ms) | Maximum | 58.4 | 46.4 | 70.4 |
|  | Max. Increase | 57.9 | 44.7 | 71.1 |
| QTc Interval (ms) | Maximum | 34.0 | 16.7 | 51.2 |
|  | Max. Increase | 34.1 | 16.1 | 52.1 |
| Heart Rate (bpm) | Minimum | −4.01 | −5.96 | −2.06 |
|  | Max. Decrease | 4.22 | 2.04 | 6.39 |

For the analyses of the maximum or minimum the predose values were considered as covariate. There was a marked prolongation in the QT and the QTc interval and a distinct decrease in heart rate indicated by the statistical analyses of the derived parameters shown above. Each of the above comparisons was statistically significant (p<0.002).

In addition to the above mentioned analyses placebo-corrected derived parameters of ECG intervals were investigated. The following table displays the means, the variation and the corresponding 95% confidence interval of the placebo-corrected derived parameters.

TABLE C

Placebo-corrected derived parameters of QT, QTc interval and heart rate

| Parameter | Derived Parameter | Mean (SD) | 95% C. I. lower | 95% C. I. upper |
|---|---|---|---|---|
| QT Interval (ms) | Maximum | 74.7 (36.7) | 56.5 | 92.9 |
|  | AUC(0–24) | 112.9 (382.9) | −77.5 | 303.3 |
| QTc Interval (ms) | Maximum | 63.9 (26.9) | 50.5 | 77.3 |
|  | AUC(0–24) | 28.5 (170.5) | −56.2 | 113.3 |
| Heart Rate (bpm) | Minimum | −15.9 (6.0) | −18.9 | −13.0 |
|  | AUC(0–24) | −13.5 (11.5) | −75.9 | 48.9 |

There was a distinct increase in the placebo-corrected QT and QTc intervals and a distinct decrease in placebo-corrected heart rate indicated by the 95% confidence intervals for the maximum (QT and QTc) and minimum (heart rate) values.

A significant effect of Tedisamil could not be found on the AUC(0-24) values. This can be explained by the chosen length of the interval. Tedisamil has a strong effect on QT, QTc and heart in the first two hours post dosing. Thus in the considered AUC(0-24) the Tedisamil effect was masked by the chosen interval.

Safety Results:

In total, seven AEs occurred in six subjects.

After treatment with Tedisamil six AEs were observed in five subjects. All AEs were judged as probably related to the study drug: injection site reaction (mild and moderate), pain injection site (2× mild, 1× moderate) and paresthesia (mild).

During treatment with placebo one AE occurred in one subject: injection site reaction with mild intensity and probable relationship to study drug.

Overall, a two-step infusion with 0.4 mg tedisamil dihydrochloride per kg body weight was well tolerated. No clinically relevant findings were observed in parameters of hematology, clinical chemistry, urinalysis and vital signs. Nevertheless there was a small increase in the arithmetic mean of systolic and diastolic blood pressure in the first four hours after dosing and a decrease in pulse rate in the first hour after dosing in the tedisamil group and almost no change in the placebo group. This outcome is consistent with the safety and tolerability results obtained in earlier studies.

Pharmacokinetic Results:

Descriptive statistics of the main pharmacokinetic parameters are given in the following Table D.

TABLE D

Descriptive statistics of the main pharmacokinetic parameters

| Parameter | Geom. Mean | 90% C. I. (lower, upper) |
|---|---|---|
| AUC(0–inf), (ng * h/ml) | 1715 | (1554, 2088) |
| AUC(0–t), (ng * h/ml) | 1670 | (1512, 2042) |
| Cmax (ng/ml) | 905 | (826, 1086) |
| t½ (h) | 5.5* | (4.88, 6.04) |
| CL (ml/min) | 315 | (284, 386) |

*Arithmetic mean

Time of peak plasma concentration ($T_{max}$) ranged between 5 and 75 minutes after start of infusion and showed a median value of 12.5 minutes.

PK/PD Modeling Results

The best-fitting pharmacokinetic model was the three-compartment constant infusion model. The PK modeling and the PK/PD modeling of this study were in close agreement with the simulations based on the PK/PD model of the single infusion study.

The variability between subjects in predicted plasma levels of Tedisamil was greater in this study than in study single infusion study.

The effect-compartment PK/PD model for infusion administration confers substantial extra predictive power for QT and QTc: correlations between the predicted tedisamil concentration in the effect compartment and QT and QTc (0.93 and 0.807 respectively) were higher than the correlations between observed plasma concentration and unadjusted QT and QTc (0.695 and 0.513 respectively).

The time-lag between plasma concentration and maximum effect was less than seen after single infusion but the difference was small.

Conclusions:

Tedisamil was safe and well tolerated following a two step infusion of 0.4 mg Tedisamil dihydrochloride per kg body weight in healthy male subjects.

The expected pharmacodynamic action of Tedisamil, i.e. a marked prolongation of QT and QTc interval and a distinct decrease in heart rate, was observed over a time period of two hours post dosing.

The PK analysis has validated the three-compartment constant infusion model for describing both single and two-step infusion pharmacokinetics, while the PK/PD analysis has validated the effect-compartment link model for describing both single and two-step infusion pharmacodynamics. Simulation studies based on these models have a good predictive value.

The following summary report of data from a conducted clinical study is giving further details on clinical efficacy results which demonstrate the usefulness of the two-step infusion.

A Multi-Center, Double-Blind, Randomized, Placebo-Controlled, Sequential Ascending Dose Groups Study to evaluate the Efficacy and Safety of Intravenous Tedisamil in the Rapid Conversion to Normal Sinus Rhythm in Patients with Atrial Fibrillation or Flutter was performed.

Drug/Dosages:

Tedisamil (0.4 mg/kg body weight)
Tedisamil (0.6 mg/kg body weight)
Placebo

Dosages were given as a 30 minute intravenous infusion regimen.

1. Study Design

This multicenter trial was a double-blind, randomized, placebo-controlled, ascending dose groups study comparing the efficacy and safety of intravenous tedisamil treatment versus placebo in symptomatic patients with atrial fibrillation or flutter (>3 hours and <48 hours). The primary efficacy endpoint of this study was the termination of atrial fibrillation or flutter (for at least 60 seconds) within 2.5 hours after start of the infusion.

The study was stratified for atrial fibrillation and atrial flutter and was conducted in two stages. The doses were given sequentially for interim safety evaluations, comparing each dose to a placebo group.

Candidates for enrollment in this study were screened from the investigator's practice and referral base.

Following screening and baseline assessments, eligible patients were randomized to tedisamil or placebo with a sequential dose escalation approach. In the first stage, patients received 0.4 mg tedisamil/kg body weight or placebo over a 30 minutes infusion period, with half the dose infused during the first 10 minutes and half the dose infused over the remaining 20 minutes. After interim safety evaluation, in the second stage, patients received 0.6 mg tedisamil/kg body weight or placebo, with the same infusion regimen.

After initiation of study drug infusion, the patient's heart rhythm was continuously monitored by telemetry for 24 hours. Digitalis and/or β-blockers or diltiazem were allowed for heart rate control during the study.

Anti-arrhythmic drugs were allowed only after 24 hours after start of infusion to avoid any potential drug interactions with tedisamil.

If clinically indicated, the investigator was allowed to restore sinus rhythm immediately following the infusion or at any time during the study by DC cardioversion according to the DC cardioversion step-up protocol. However, DC cardioversion within 2.5 hours after initiation of the infusion was strongly discouraged.

Patients were discharged from the telemetry unit 24 hours post infusion and safety follow up was to be obtained after 28 days. Blinded reviews of 12-lead ECGs (including seconds rhythm strip) and 24 hour Holters to adjudicate the clinical endpoint (conversion to normal sinus rhythm) were performed centrally according to standard guidelines.

Figure 1:
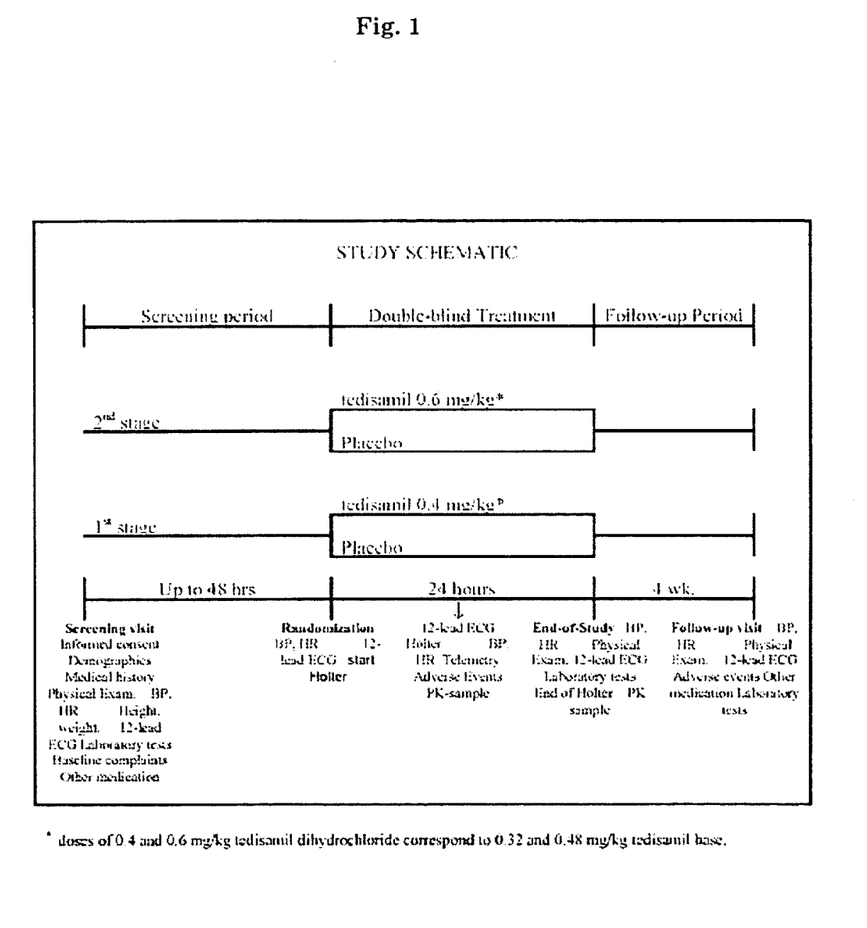
FIG. 1 depicts a flowchart concerning a study related to certain embodiments of the invention.

FIG. 1: A study flowchart is given in FIG. 1.

2. Study Objectives 2.1 Primary Efficacy Objective

The primary objective of the study was to demonstrate the superiority of any dose of tedisamil to placebo in the termination of atrial fibrillation/flutter as measured by the percentage of patients converted to normal sinus rhythm (NSR) (for at least 60 seconds) at any time within 2.5 hours after the start of infusion.

2.2 Secondary Efficacy Objectives

Secondary efficacy objectives were:

To determine the percentage of patients converted to normal sinus rhythm (for at least 60 seconds) at any time within 2.5 hrs and remaining in sinus rhythm until 2.5 hours after initiation of the intravenous infusion of tedisamil versus placebo.

To determine the percentage of patients converted to normal sinus rhythm (for at least 60 seconds) at any time within 24 hours after initiation of the intravenous infusion of tedisamil versus placebo.

To determine the percentage of patients converted to normal sinus rhythm (for at least 60 seconds) at any time within 24 hrs and remaining in sinus rhythm until 24 hours after initiation of the intravenous infusion of tedisamil versus placebo.

To determine the percentage of patients converted to normal sinus rhythm (for at least 60 seconds) at any time within 2.5 hrs and remaining in sinus rhythm until 24 hours after initiation of the intravenous infusion of tedisamil versus placebo.

To determine the time to conversion after the start of the infusion of tedisamil versus placebo.

To determine the dose- and concentration-response relationships of tedisamil versus placebo.

2.3 Safety Objective

The safety objective was: To determine the safety and tolerability of tedisamil versus placebo.

3. Iclusion and Exclusion Criteria 3.1 Inclusion Criteria

Willing to sign informed consent before screening examinations are performed and before the study drug is administered.

Male or female, >18 years of age.

Patients with documented (60 seconds rhythm strip) symptomatic atrial fibrillation or flutter (duration >3 hours and <48 hours) at the time of randomization, occurring either as a first episode or as a recurrent episode. Atrial fibrillation or flutter is considered recurrent if a prior episode is documented, and had either terminated spontaneously or had been successfully treated by drugs or by direct-current (DC) cardioversion. At the time of randomization patients must exhibit atrial fibrillation or flutter.

Patients who are hemodynamically stable (supine systolic blood pressure >90 mmHg and diastolic blood pressure <105 mmHg).

3.2 Exclusion Criteria

Patients were to be excluded from the study for any of the following reasons:

Any woman who is pregnant, lactating, or not using medically acceptable contraception.

All women of childbearing potential who are not surgically sterilized must have documented negative serum pregnancy test done at the screening visit and be practicing a medically acceptable contraceptive method (e.g., tubal ligation, birth control pills, or any barrier methods) for at least 3 calendar months prior to randomization. Women of childbearing age must have no intention of becoming pregnant during the study period.

Evidence of severe hematologic, immunologic, respiratory, urogenital, gastrointestinal, hepatic, renal, endocrinologic, metabolic, nutritional, psychiatric, dermatologic, connective tissue, musculoskeletal, malignant or other relevant disease, allergy or surgery, as revealed by history, physical examination and/or laboratory assessments which may limit participation in or prevent completion of the study.

Clinical evidence of hyperthyroidism.

Demonstrated atrial or ventricular thrombus or valvular vegetation during trans-esophageal echocardiogram.

History of a cerebrovascular accident within 6 months prior to randomization.

Congestive heart failure of NYHA functional Class III. IV.

Acute coronary syndromes at the time of randomization.

Known history and/or electrocardiographic evidence of ventricular pre-excitation.

History of life-threatening ventricular arrhythmias including Torsade de Pointes.

Previous electrocardiographic evidence of second- or third-degree AV block.

Ventricular rate <50 bpm or >200 bpm documented by 12-lead ECG.

Myocardial infarction within 30 days prior to randomization.

Cardiac surgery within 3 months prior to randomization.

Stent placement or PTCA within 30 days prior to randomization.

Congenital long QT syndrome.

QT interval >470 ms prior to randomization.

Plasma creatinine >1.8 mg/dl

Serum potassium <4.0 mEq/L.

Evidence of digitalis intoxication.

Concurrent treatment with anti-arrhythmic drugs (except for digitalis, diltiazem or β-blockers), not discontinued 5 half-lives before randomization.

Treatment with amiodarone within 3 months prior to randomization.

Participation in a previous tedisamil clinical study.

Participation in a clinical trial and/or intake of an investigational drug within four weeks prior to the screening visit.

Any history of drug abuse, including alcohol, within one year of screening visit.

Serious drug allergy or any history of serious abnormal drug reaction.

4. Concomitant Medication

Concomitant use of Class-I or Class-III anti-arrhythmic medication were not allowed. Class-I or Class-III anti-arrhythmic medications were to be discontinued more than five elimination half-lives prior to randomization. Amiodarone was to be discontinued for three months prior to randomization. Furthermore, verapamil and any potentially PR prolonging drug were not allowed. Allowed medications included anticoagulants, warfarin and other coumarin derivates, heparin, antihypertensive agents including potassium sparing diuretics (alone or combination with other diuretics), β-blockers (except Sotalol), dihydropyridine calcium channel blockers and diltiazem, aspirin, digoxin and digitoxin.

5. Test Product, Dose and Mode of Administration

Tedisamil dihydrochloride, 0.4 mg/kg body weight, 0.6.mg/kg body weight was administered intravenously. The total infusion time was 30 minutes, with half the dose infused within 10 minutes, and half the dose infused within the remaining 20 minutes.

Matching placebo was given intravenously.

6. Criteria for Evaluation 6.1 Efficacy 6.1.1 Primary Efficacy

The percentage of patients converted to normal sinus rhythm (for at least 60 seconds) at any time within 2.5 hours after the initiation of the infusion of study drug.

6.1.2 Secondary Efficacy

The percentage of patients converted to normal sinus rhythm (for at least 60 seconds) at any time within 2.5 hrs and remaining in sinus rhythm until 2.5 hours after initiation of the intravenous infusion of tedisamil versus placebo.

The percentage of patients converted to normal sinus rhythm (for at least 60 seconds) at any time within 24 hours after initiation of the intravenous infusion of tedisamil versus placebo.

The percentage of patients converted to normal sinus rhythm (for at least 60 seconds) at any time within 24 hrs and remaining in sinus rhythm until 24 hours after initiation of the intravenous infusion of tedisamil versus placebo.

The percentage of patients converted to normal sinus rhythm (for at least 60 seconds) at any time within 2.5 hrs and remaining in sinus rhythm until 24 hours after initiation of the intravenous infusion of tedisamil versus placebo.

The time to conversion after the start of the infusion of tedisamil versus placebo.

The dose- and concentration-response relationships of tedisamil versus placebo.

6.2 Safety

Safety was monitored regarding: Physical examination, ECG, 24-hour Holter monitoring, vital signs, laboratory evaluations and adverse events.

7. Statistical Methods

The intent-to-treat patient sample was analyzed for efficacy. All tests were two-sided and a p-value <0.05 was considered significant. Differences in percentages of conversion were compared among the treatment groups using the Pearson chi-square statistic. Safety analysis was conducted on the safety patient sample. Numbers and percentages of patients with adverse events were calculated for each treatment group, using MedDRA preferred terms and body systems. Descriptive statistics were summarized by treatment group for changes from baseline in QT, heart rate and blood pressure.

8. Patient Population 8.1 Number of Patients

Overall, 203 patients signed informed consent, 200 patients were randomized, 20 patients did not receive study medication. The analyses were based on two samples, the safety sample and the intention-to-treat sample.

8.1.1 Safety Sample 180 patients were included in the safety sample: 61 in the placebo group, 65 in the tedisamil 0.4 mg/kg group (henceforth, 0.4 mg group), and 54 in the tedisamil 0.6 mg/kg group (henceforth, 0.6 mg group).

8.1.2 Intention-to-Treat Sample 175 patients were included in the intention-to-treat sample: 59 in the placebo group, 63 in the 0.4 mg group, and 53 in the 0.6 mg group. From 180 patients who were randomized and received trial medication, 5 patients did not have efficacy measurements (ECGs and Holter) after start of infusion, thus they had to be excluded from the ITT sample.

9. Efficacy Results 9.1 Demographics

Overall, 62% of patients were male and 38% female in this study; average age was 63 years (range 29–87). 45% of patients were on beta-blocker treatment. 81% of patients had atrial fibrillation and 19% had atrial flutter at randomization. 63% of patients had NYHA class I and 34% had NYHA class II congestive heart failure. The mean duration of atrial fibrillation or flutter was 24 hrs. 63% of patients had atrial fibrillation or atrial flutter as a recurrent episode. The mean time since the first documented episode of atrial fibrillation or atrial flutter was 2.3 yrs. None of the differences between treatment groups in demographic data were large enough to be of clinical relevance.

9.2 Primary Efficacy Parameter

The percentage of patients converted to normal sinus rhythm (for at least 60 seconds) at any time within 2.5 hours after the initiation of the infusion of study drug for patients with atrial fibrillation was 9% (N=4) in the placebo group and 46% (N=24) and 57% (N=24) in the tedisamil 0.4 mg and 0.6 mg group respectively. The treatment comparison versus placebo was statistically significant for both treatment groups (p<0.001).

The percentage of patients converted to normal sinus rhythm (for at least 60 seconds) at any time within 2.5 hours after the initiation of the infusion of study drug for patients with atrial flutter was 0% in the placebo group, and 11% and 27% in the tedisamil 0.4 mg and 0.6 mg group respectively. The treatment comparison versus placebo was statistically significant for the tedisamil 0.6 mg dose group (p=0.044). The. percentage of patients converted to normal sinus rhythm (for at least 60 seconds) at any time within 2.5 hours after the initiation of the infusion of study drug for patients with atrial fibrillation taking beta-blockers was 7% (N=1) in the placebo group, and 52% (N=14) and 60% (N=12) in the tedisamil 0.4 mg and 0.6 mg group respectively.

9.3 Secondary Efficacy Parameter

The results for the primary and selected secondary efficacy parameters are described in the tables 1 and 2 below:

TABLE 1

| | Patients with atrial fibrillation | | |
| --- | --- | --- | --- |
| | Tedisamil | | |
| Parameter | 0.4 mg/kg | 0.6 mg/kg | Placebo |
| Conversion to NSR at any time within 2.5 hrs after the start of infusion | 24 out of 52 (46%) | 24 out of 42 (57%) | 4 out of 46 (9%) |
| p-value, Pearson ChiSq (vs placebo) | <0.001 | <0.001 | |
| Conversion to NSR at any time within 2.5 hrs and remaining in NSR until 2.5 hrs after the start of infusion | 23 out of 52 (44%) | 24 out of 42 (57%) | 4 out of 46 (9%) |
| p-value, Pearson ChiSq (vs placebo) | <0.001 | <0.001 | |

TABLE 1-continued

Patients with atrial fibrillation

| Parameter | Tedisamil 0.4 mg/kg | Tedisamil 0.6 mg/kg | Placebo |
|---|---|---|---|
| Conversion to NSR at any time within 24 hrs after the start of infusion | 26 out of 42 (62%) | 26 out of 37 (70%) | 12 out of 34 (35%) |
| p-value, Pearson ChiSq (vs placebo) | 0.021 | 0.003 | |
| Conversion to NSR at any time within 24 hrs and remaining in NSR until 24 hrs after the start of infusion | 24 out of 42 (57%) | 24 out of 37 (65%) | 12 out of 34 (35%) |
| p-value, Pearson ChiSq (vs placebo) | 0.058 | 0.013 | |
| Conversion to NSR at any time within 2.5 hrs and remaining in NSR until 24 hrs after the start of infusion | 22 out of 42 (52%) | 22 out of 37 (59%) | 4 out of 34 (12%) |
| p-value, Pearson ChiSq (vs placebo) | <0.001 | <0.001 | |

TABLE 2

Patients with atrial flutter

| Parameter | Tedisamil 0.4 mg/kg | Tedisamil 0.6 mg/kg | Placebo |
|---|---|---|---|
| Conversion to NSR at any time within 2.5 hrs after the start of infusion | 1 out of 9 (11%) | 3 out of 11 (27%) | 0 out of 13 (0%) |
| p-value, Pearson ChiSq (vs placebo) | 0.219 | 0.044 | |
| Conversion to NSR at any time within 2.5 hrs and remaining in NSR until 2.5 hrs after the start of infusion | 1 out of 9 (11%) | 3 out of 11 (27%) | 0 out of 13 (0%) |
| p-value, Pearson ChiSq (vs placebo) | 0.219 | 0.044 | |
| Conversion to NSR at any time within 24 hrs after the start of infusion | 2 out of 7 (29%) | 3 out of 7 (43%) | 1 out of 7 (14%) |
| p-value, Pearson ChiSq (vs placebo) | 0.515 | 0.237 | |
| Conversion to NSR at any time within 24 hrs and remaining in NSR until 24 hrs after the start of infusion | 2 out of 7 (29%) | 3 out of 7 (43%) | 1 out of 7 (14%) |
| p-value, Pearson ChiSq (vs placebo) | 0.515 | 0.237 | |
| Conversion to NSR at any time within 2.5 hrs and remaining in NSR until 24 hrs after the start of infusion | 1 out of 7 (14%) | 3 out of 7 (43%) | 0 out of 7 (0%) |
| p-value, Pearson ChiSq (vs placebo) | 0.299 | 0.051 | |

The results according to the present invention, e.g., of the randomized placebo-controlled study, demonstrate that intravenously administered tedisamil is effective in the acute conversion of patients with atrial fibrillation or flutter of up to 48 hours duration. There was a conversion rate of 46% observed with 0.4 mg/kg tedisamil and of 57% at a dose 0.6 mg/kg. There was a rapid onset of action with an average time to cardioversion of 35 minutes after the start of tedisamil administration.

10. Conclusions

The results for the primary and secondary efficacy parameters indicated a dose dependent and statistically significant difference between placebo and both, tedisamil 0.4 mg/kg and tedisamil 0.6 mg/kg in the rapid conversion of atrial fibrillation into normal sinus rhythm. The results for patients with atrial flutter were statistically significant for the high dose group.

In summary, tedisamil given as a two-step infusion regimen has shown to be effective in conversion of atrial fibrillation and flutter to NSR. Tedisamil was well tolerated, no sustained polymorphic VT were observed, no patient required DC cardioversion for treatment of VTs.

A two step infusion regimen for rapid conversion of recent onset atrial fibrillation/flutter to normal sinus rhythm may be in particular beneficial in male patients.

A) Phase II Clinical Study

The analysis of a first study showed surprisingly that there is a gender difference related to efficacy, e.g. that male patients show a higher conversion rate compared to women when treated with tedisamil. Furthermore, the male patients show less safety issues than female patients. Hence, it was surprisingly found that tedisamil as compared to female patients shows specificity for male patients in anti-arrhythmic treatment, and in particular in conversion of recent onset of atrial fibrillation (Afib) to normal sinus rhythm (NSR).

This first clinical study was a Multi-Center, Double-Blind, Randomized, Placebo-Controlled, Sequential Ascending Dose Groups Study to evaluate the Efficacy and Safety of Intravenous Tedisamil in the Rapid Conversion to Normal Sinus Rhythm in Patients with Atrial Fibrillation or Flutter. The active ingredient used was tedisamil dihydrochloride. The study was designed as a phase II study and executed in 35 to 40 centers in 3 to 4 countries. Study duration: Screening: up to 48 hours; treatment (in-patient): single 30-minute infusion; safety follow up: 24 hours (in-patient) with continuous telemetry and 28 day safety follow up.

The primary efficacy objective of the study was to demonstrate the superiority of any dose of tedisamil to placebo in the termination of atrial fibrillation/flutter as measured by the percentage of patients converted to normal sinus rhythm (NSR) (for at least 60 seconds) at any time within 2.5 hours after the start of infusion. Secondary efficacy objectives were to determine the percentage of patients remaining in sinus rhythm at 2.5 hours after initiation of the intravenous infusion of tedisamil versus placebo; to determine the percentage of patients remaining in sinus rhythm at 24 hours after initiation of the intravenous infusion of tedisamil versus placebo; to determine the time to conversion after the start of the infusion of tedisamil versus placebo; and to determine the dose- and plasma concentration-response relationships of tedisamil versus placebo. Safety objective: determining the safety and tolerability of tedisamil versus placebo.

The following methodology was applied: A multi-center, double-blind, randomized, placebo-controlled, sequential ascending dose groups study to evaluate the efficacy and safety of intravenous tedisamil versus placebo. The study drug was infused over 30 minutes, receiving half the dose within 10 minutes and half the dose within the remaining 20 minutes. The first patient group received 0.4 mg/kg body-weight (bw), infused as 0.2 mg/kg bw within 10 minutes, continued with 0.2 mg/kg bw infused within 20 minutes. The next higher dose 0.6 mg/kg bw (0.3 mg/kg bw infused within 10 min, continued with 0.3 mg/kg bw infused within 20 minutes) was only administered after the initial dose has been assessed (blinded) and found to be safe. A third stage may be added with a higher dose. Tedisamil blood concentrations were assessed during the infusion (at 10 and 30 minutes), at conversion to normal sinus rhythm, at recurrence and 24 hours after start of infusion.

Planned number of subjects: 330 randomized (110 patients per dose group)

Diagnosis and Main Criteria for Inclusion:

Atrial fibrillation or flutter with a duration of >3 hours and <48 hours, occurring as a first or recurrent episode.

Test Product, Dose and Mode of Administration:

Tedisamil (0.4 mg/kg body weight)

Tedisamil (0.6 mg/kg body weight)

Both dosages were given as an intravenous regimen

Reference Therapy, Dose and Mode of Administration:

Placebo (vehicle) administered as a 30-minute intravenous infusion.

Duration of Treatment:

The total infusion time is 30 minutes, with half the dose infused within 10 minutes, and half the dose infused within the remaining 20 minutes.

Criteria for Evaluation:

1) Efficacy:

Primary efficacy: the percentage of patients converted to normal sinus rhythm (for at least 60 seconds) at any time within 2.5 hours after the initiation of the infusion of study drug.

Secondary efficacy: percentage of patients in NSR at 2.5 and 24 hours after start of infusion; time to conversion; dose- and concentration-response relationships.

2) Safety:

Physical examination, ECG, 24-hour Holter monitoring, vital signs, laboratory evaluations and adverse events.

Statistical Methods:

All efficacy variables were evaluated separately for patients with atrial fibrillation and patients with atrial flutter. Percentages of conversion were compared among treatment groups using a logistic regression model with factors for treatment group and center. Times to conversion were compared among treatment groups using a Cox proportional hazards model with factors for treatment group and center. Dose-response and concentration-response relationships were examined using descriptive statistics.

For the calculation of the number of patients the following assumptions were made:
1. For atrial fibrillation patients, the percentage of conversion to normal sinus rhythm (at any time within 2.5 hours after the initiation of the infusion) in the placebo group is equal to 20% and the clinically relevant difference is 20%.
2. For atrial flutter patients, the percentage of conversion to normal sinus rhythm in the placebo group is equal to 10% and the clinically relevant difference is 40%.

Interim analyses for efficacy was performed halfway the first and second stages by an external statistician. The purpose is to terminate a stage when the tedisamil dose used in that stage is inefficacious. Technically, each interim analysis was a predictive power calculation for the comparison of tedisamil and placebo with respect to the primary efficacy variable. Blinded safety reviews were performed at the same time as the efficacy analyses and, in addition, at the end of the each stage (if applicable).

B) Phase III Clinical Study

The analysis of a second study confirmed the finding of the first study, e.g. that there is a gender difference related to efficacy, e.g. that male patients show a higher conversion rate compared to women when treated with tedisamil.

This second clinical study was a Multi-Center, Double-Blind, Randomized, Placebo-Controlled, Parallel Design Study to evaluate the Efficacy and Safety of Intravenous Tedisamil Sesquifumarate in the Rapid Conversion to Normal Sinus Rhythm in Subjects with Recent Onset Atrial Fibrillation or Flutter.

The active ingredient used was tedisamil sesqifumarate. The study was designed as a phase II study and executed in 30 to 40 centers in 5 countries. Study duration: Screening: up to 48 hours; treatment (in-patient): single 30-minute infusion; safety follow up: 24 hours (in-patient) with continuous telemetry and 28 day safety follow up.

The primary efficacy objective of the study was to demonstrate the superiority of any dose of tedisamil sesquifumarate to placebo in the rapid conversion to normal sinus rhythm (for at least 60 seconds), as measured by the percentage of subjects converted at any time within 2.5 hours after the start of infusion. Secondary efficacy objectives were to determine the percentage of subjects converting to normal sinus rhythm at any time within 2.5 hours after start of the intravenous infusion and in normal sinus rhythm at 2.5 hours after initiation of the infusion of tedisamil sesquifumarate versus placebo; to determine the percentage of subjects converting to normal sinus rhythm at any time within 2.5 hours after start of the intravenous infusion and in normal sinus rhythm at 24 hours after initiation of the infusion of tedisamil sesquifumarate versus placebo; to determine the percentage of subjects converting to normal sinus rhythm at any time within 2.5 hours after start of the intravenous infusion and in normal sinus rhythm at hospital discharge; to determine the time to conversion to normal sinus rhythm after the start of the infusion of tedisamil sesquifumarate versus placebo; to determine the dose- and concentration-response relationships of tedisamil sesquifumarate versus placebo; and to determine the energy required for DC cardioversion of tedisamil sesquifumarate versus placebo. Safety objective: determining the safety and tolerability of tedisamil sesquifumarate versus placebo.

The following methodology was applied: A multi-center, double-blind, randomized, placebo-controlled study to evaluate the efficacy and safety of intravenous tedisamil sesquifumarate versus placebo. The study drug was infused over 30 minutes, receiving half the dose within 10 minutes and half the dose within the remaining 20 minutes. Subjects were randomly assigned to receive either:

0.32 mg tedisamil free base per kg bodyweight (bw) (0.16 mg/kg bw within 10 minutes, followed by 0.16 mg/kg bw within 20 minutes); or 0.48 mg tedisamil free base per kg bw (0.24 mg/kg bw within 10 min, followed by 0.24 mg/kg bw within 20 minutes); or 0.64 mg tedisamil free base per kg bw (0.32 mg/kg bw within 10 min, followed by 0.32 mg/kg bw within 20 minutes); or a 30 minute placebo infusion.

Planned Number of Subjects:

212 randomized atrial fibrillation subjects (53 subjects per treatment group). These subjects are the primary target population. In addition, 80 (20 per treatment group) subjects with atrial flutter considered to be enrolled within the scope of this study. However, the study could be terminated without all atrial flutter subjects enrolled if the planned number of atrial fibrillation subjects has been reached.

Diagnosis and Main Criteria for Inclusion:
  Atrial fibrillation or flutter with a duration of >3 hours and <45 days, occurring as a first or recurrent episode.
Test Product, Dose and Mode of Administration:
  Tedisamil free base 0.32 mg/kg body weight (equivalent to 0.51 mg/kg tedisamil sesquifumarate and to 0.4 mg/kg tedisamil dihydrochloride)
  Tedisamil free base 0.48 mg/kg body weight (equivalent to 0.77 mg/kg tedisamil sesquifumarate and to 0.6 mg/kg tedisamil dihydrochloride)
  Tedisamil free base 0.64 mg/kg body weight (equivalent to 1.02 mg/kg tedisamil sesquifumarate and to 0.8 mg/kg tedisamil dihydrochloride)
  The dosages will be given as an intravenous regimen.
  Tedisamil doses in the protocol refer to tedisamil free base.
Reference Therapy, Dose and Mode of Administration:
  Placebo (vehicle) administered as a 30-minute intravenous infusion similar to tedisamil infusion.
Duration of Treatment:
  The total infusion time is 30 minutes, with half the dose infused within 10 minutes, and half the dose infused within the remaining 20 minutes.
Criteria for Evaluation:
  1) Efficacy:
  Primary efficacy: the percentage of subjects converted to normal sinus rhythm (for at least 60 seconds) at any time within 2.5 hours after the initiation of the infusion of study drug.
  Secondary efficacy: percentage of subjects in normal sinus rhythm at any time within 2.5 hours and at 24 hours after start of infusion, as well as at hospital discharge, time to conversion, dose- and concentration-response relationships and DC cardioversion energy.
  2) Safety:
  Physical examination, ECG, 24-hour Holter monitoring, vital signs, laboratory evaluations and adverse events.
Statistical Methods:
  Percentages of conversion will be compared among treatment groups using the (Pearson) chi-square statistics. Times to conversion will be compared among treatment groups using the log-rank test. Dose-response and concentration-response relationships and the energy required for DC conversion will be examined using descriptive statistics.
  Subjects with atrial fibrillation and atrial flutter will be separately analyzed. In addition, both populations will be pooled for analysis. All analyses involving the atrial flutter subject population will be considered as exploratory.

TABLE I

Conversion of recent onset of atrial fibrillation (Afib) to NSR
Conversion to NSR at any time within 2.5 hrs after start of infusion.
ITT patient sample; patients with DC cardioversion are excluded.

| | | Anti-arrhythmic Treatment with | | |
| | | Tedisamil | | |
| | Gender | 0.4 mg/kg | 0.6 mg/kg | Placebo |
|---|---|---|---|---|
| Atrial Fibrillation | Male | 18/35 (51.4%) | 18/26 (69.2%) | 2/24 (8.3%) |
| | Female | 6/17 (35.3%) | 6/16 (37.5%) | 2/22 (9.1%) |
| Atrial Flutter | Male | 1/7 (14.3%) | 1/5 (20.0%) | 0/10 |
| | Female | 0/2 | 2/6 (33.3%) | 0/3 |
| Overall | Male | 19/42 (45.2%) | 19/31 (61.3%) | 2/34 (5.9%) |
| | Female | 6/19 (31.6%) | 8/22 (36.4%) | 2/1 (8.0%) |

TABLE II

Conversion of recent onset of atrial fibrillation (Afib) to NSR
Conversion to NSR at any time within 2.5 hrs after start of infusion.
Patients with atrial fibrillation ITT patient sample;
patients with DC cardioversion are excluded.

| | | Anti-arrhythmic Treatment with | | |
| | | Tedisamil | | |
| Gender | Age | 0.4 mg/kg | 0.6 mg/kg | Placebo |
|---|---|---|---|---|
| Male | <65 yrs | 10/20 (50.0%) | 13/18 (72.2%) | 1/14 (7.1%) |
| | >=65 yrs | 8/15 (51.4%) | 5/8 (62.5%) | 1/10 (10%) |
| | Total | 18/35 (51.4%) | 18/26 (69.2%) | 2/24 (8.3%) |
| Female | <65 yrs | 2/5 (40.0%) | 1/3 (33.3%) | 1/5 (20.0%) |
| | >=65 yrs | 4/12 (33.3%) | 5/13 (38.5%) | 1/17 (5.9%) |
| | Total | 6/17 (35.3%) | 6/16 (37.5%) | 2/22 (9.1%) |

TABLE III

Conversion of recent onset of atrial fibrillation (Afib) to NSR
Conversion to NSR at any time within 2.5 hrs after start of infusion.
ITT patient sample; patients with DC cardioversion are excluded.

| | | Anti-arrhythmic Treatment with | | |
| | | Tedisamil | | |
| | Gender | 0.4 mg/kg | 0.6 mg/kg | Placebo |
|---|---|---|---|---|
| Atrial Fibrillation | Male | 18/35 (51.4%) | 18/26 (69.2%) | 2/24 (8.3%) |
| | p-value, ChiSq (vs placebo) | <0.001 | <0.001 | |
| | Female | 6/17 (35.3%) | 6/16 (37.5%) | 2/22 (9.1%) |
| | p-value, ChiSq (vs placebo) | <0.045 | <0.034 | |
| Atrial Flutter | Male | 1/7 (14.3%) | 1/5 (20.0%) | 0/10 |
| | p-value, ChiSq (vs placebo) | 0.218 | 0.143 | |
| | Female | 0/2 | 2/6 (33.3%) | 0/3 |
| | p-value, ChiSq (vs placebo) | — | 0.17 | |
| Overall | Male | 19/42 (45.2%) | 19/31 (61.3%) | 2/34 (5.9%) |
| | p-value, ChiSq (vs placebo) | <0.001 | <0.001 | |
| | Female | 6/19 (31.6%) | 8/22 (36.4%) | 2/1 (8.0%) |
| | p-value, ChiSq (vs placebo) | <0.045 | <0.018 | |

It can be seen from these data that the anti-arrhythmic male patients respond to the treatment with tedisamil more specifically than female patients in the anti-arrhythmic treatment, and in particular in the conversion of recent onset of atrial fibrillation (Afib)/flutter to normal sinus rhythm (NSR).

What is particularly surprising is the effectiveness of 3,7-diazabicyclo-[3,3,1]-nonane compounds, preferably of 9,9-alkylene-3,7-diazabicyclo [3,3,1]-nonane compounds, and most preferably of tedisamil, and of pharmaceutically acceptable acid addition salts and/or solvates in male patients, as proved by the above results of the studies, in the treatment and/or inhibition of anti-arrhythmic events in male patients, in particular in the conversion of recent onset of atrial fibrillation (Afib) to NSR in male patients, since such gender difference related to efficacy has never been observed before in a vast variety of investigations with tedisamil in both genders.

From the results regarding efficacy of tedisamil found in the studies it may be summarized that tedisamil-like 3,7-diazabicyclo-[3,3,1]nonane compounds, preferably of 9,9-alkylene-3,7-diazabicyclo[3,3,1]-nonane compounds, and most preferably tedisamil itself, as well,as the acid addition salts, show higher conversion rates in male patients as compared to female patients. Extension of infusion beyond the times indicated above did not produce higher conversion rates. From the results it may be summarized regarding safety: Almost all observed TdP (Torsade de Point) in 30 min regimen were in female patients. Only one male showed TdP with high dosage on 0.72 in the study. Liquid Pharmaceutical Formulations.

As a therapeutic agent, 3,7-diazabicyclo-[3,3,1]nonane compounds, preferably of 9,9-alkylene-3,7-diazabicyclo[3,3,1]-nonane compounds, and most preferably of tedisamil, and of pharmaceutically acceptable acid addition salts and/or solvates, may be contained together with any conventional and/or newly developed pharmaceutical galenical ingredient suitable for the use in i.v. injections and infusions such like excipient, liquid carrier, auxiliary, and/or adjuvant in the liquid pharmaceutical formulations according to the present invention. Examples of liquid formulations are such as solutions, suspensions or emulsions, liposomes, solid lipid nano-particles and any other conventional and/or novel drug delivery system suitable for i.v. injection or infusion of in particular 3,7-diaza-bicyclo-[3,3,1]nonane compounds, preferably of 9,9-alkylene-3,7-diazabicyclo[3,3,1]-nonane compounds, and most preferably of tedisamil, and of pharmaceutically acceptable acid addition salts and/or solvates and/or prodrugs thereof. Infusions are e.g. sterile, aqueous solutions or emulsions with water as the continuous phase; they are usually made isotonic with blood. They are principally intended for administration in large volume.

The liquid formulations may contain usual diluents such as water, oils and/or lipids, organic solvent or co-solvents, suspension agents and the like. Also other conventional and/or novel auxiliaries, suitable for the use in i.v. injections and in particular for infusions, may additionally be added, such as preservatives, stabilizers, anti-oxidants, pH adjustments, buffers, adjuvants for adjustment of e.g. tonicity or adjustment of viscosity, antibacterial and/or antifungal agents, e.g. parabene, chlorobutanol, phenol, sorbic acid and the like. Preferably the liquid pharmaceutical formulations are suitable for infusion regimens, e.g. for intravenous infusion. The ingredients, techniques and the procedures required to manufacture liquid pharmaceutical formulations of an active agent are well known to the skilled person.

The 3,7-diazabicyclo-[3,3,1]nonane compounds, preferably of 9,9-alkylene-3,7-diazabicyclo[3,3,1]-nonan compounds, and most preferably tedisamil, and pharmaceutically acceptable acid addition salts and/or solvates and/or prodrugs thereof, can be mixed and formulated with the pharmaceutical excipients, auxiliaries liquid carriers and/or adjuvants in known manner. For example, the ingredients like the active compound and the required liquid pharmaceutical excipients or carriers and the desired auxiliaries and adjuvants etc. may be mixed together, optionally lyophilized, and e.g. a resulting solution, emulsion, suspension or liposomes may be filled into suitable primary packing materials, e.g. vials, ampules, containers, infusion pouches or dual chamber systems suited for infusion purposes, and may additionally be sterilized. Usually, infusion solutions must be prepared with enhanced care; in particular the solution must be isotonic or at least approximately isotonic. The adjustment of pH is usually arranged by addition of hydrochloric acid or sodium hydroxide. Infusions should be isotonic or approximately isotonic, e.g. iso-osmotic or approximately iso-osmotic. For adjusting e.g. hypo-osmotic solutions sodium chloride, glucose or mannitol may be added to arrange for iso-osmotic conditions. Eventually a compromise is necessary regarding isotonic condition, euhydric condition, physiological requirements and stability of the active agent. Stabilisation and or sterilisation may be suitable. In the manufacture of infusions containing dispersed particles, measures are taken to ensure a suitable and controlled particle size with regard to the intended use. The volume of the infusion in the container is sufficient to permit the withdrawal and administration of the nominal dose using a normal technique. Suitable methods for the preparation of infusions, the ingredients and conditions to be met are well known to the skilled artisan, e.g. from monographs and/or pharmacopeias such as the European pharmacopoeia or the US pharmacopoeia.

According to a particular aspect of the invention the liquid pharmaceutical is suited for administration by infusion, in particular by intravenous infusion. The person skilled in that art is aware of how to prepare infusion and/or i.v. injection solutions and which conditions are to be met, or how infusions are to be administered to a patient. Infusions may be prepared from concentrates for injections or infusions. Concentrates for injections or infusions are sterile solutions intended for injection or infusion after dilution. They are diluted to a prescribed volume with a prescribed liquid before administration. After dilution, they comply with the requirements for injections or for infusions. Infusions may be also prepared from solid powders for injections or infusions which are solved in the required amount of a suitable sterile solvent just before the administration to the patient. Powders for injections or infusions are solid, sterile substances distributed in their final containers and which, when shaken with the prescribed volume of a prescribed sterile liquid, rapidly form either clear and practically particle-free solutions or uniform suspensions. After dissolution or suspension, they comply with the requirements for injections or for infusions. Freeze-dried products for parenteral use usually are considered as powders for injections or infusions.

Intravenous administration allows rapid administration of larger volumes. The advantage of infusion is e.g. rapid onset of the pharmaceutically effect of the active agent, in particular in emergency situations. For example, the infusion may be administered as a rapid infusion during the first step or phase of the administration, and then followed by dropwise intravenous infusion by which over the period of administration constant blood levels of the drug may be achieved and/or maintained. Administration may be also by dual chamber systems, e.g. to avoid drug instability prior administration.

EXAMPLES

The following Example describes a liquid pharmaceutical formulation which contains an active substance of Formula I according to the invention, and also the production of such pharmaceutical preparations. The following example explains the production of a liquid pharmaceutical preparation containing tedisamil dihydrochloride. Liquid pharmaceutical preparations containing tedisamil sesquifumarate may be obtained in an analogous manner.

Example

Ampules Composition (per ampule)

| | |
|---|---|
| 5 mg | N,N'-dicyclopropylmethyl-9,9-tetramethylen-3,7-diazabicyclo[3,3,1]nonane dihydrochloride |
| 16 mg | Sodium chloride |

Water for injection purposes to make up to 2.0 ml

Preparation Method

Sodium chloride was dissolved in water for injection purposes. The active substance was added and dissolved while stirring. Sufficient water for injection purposes was added to make up the final volume. The mixture was passed through a 0.1 μm membrane filter. 2.15 ml aliquots were filled into brown glass ampules, and the ampules were hermetically closed. The ampules were sterilized with steam for 30 minutes at 121° C. 2 ml of the resulting injection solution contained 5 mg of the active substance.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method of treating an arrhythmic event in a human patient suffering therefrom, said method comprising administering to said patient by continuous infusion a single dose of an effective arrhythmia inhibiting amount of at least one 3,7-diazabicyclol[3,3,1]nonane compound or a physiologically acceptable acid addition salt thereof, wherein the continuously administered single dose is administered in a two successive phases, such that in the first phase a first part of the continuously administered single dose is administered at a first rate, and in the second phase a second part of the continuously administered single dose is administered at a second, slower rate.

2. The method of claim 1, wherein said arrhythmic event is onset of atrial fibrillation or flutter and said method results in conversion of atrial fibrillation or flutter to normal sinus rhythm.

3. The method of claim 1, wherein said compound is present as a solvate or as a prodrug.

4. The method of claim 1, wherein said compound corresponds to Formula I:

wherein
R1 represents an alkyl group containing from 1 to 6 carbon atoms; an alkylene group containing from 3 to 6 carbon atoms having a double bond which is not linked directly to the nitrogen atom; a cycloalkylalkyl group containing from 4 to 9 carbon atoms or a benzyl group;
R2 represents a lower alkyl group;
R3 represents a lower alkyl group or
R2 and R3 together form an alkylene chain containing from 3 to 6 carbon atoms; and
R4 represents an alkyl group containing from 1 to 6 carbon atoms; an alkenyl group containing from 3 to 6 carbon atoms having a double bond which is not linked directly to the nitrogen atom; a cycloalkylalkyl group containing from 4 to 9 carbon atoms; a group corresponding to Formula a:

wherein
R5 represents hydrogen, halogen, lower alkyl or lower alkoxy, and
Z represents an alkylene chain containing from 1 to 3 carbon atoms;
a propenylene chain having a double bond which is conjugated with the phenyl group; or
a group corresponding to Formula b:

wherein
R6 represents hydrogen, halogen, lower alkyl or lower alkoxy and
R7 represents hydrogen, halogen, lower alkyl or lower alkoxy.

5. The method of claim 4, wherein R1 represemts an alkyl group containing from 1 to 6 carbons atoms or a cycloalkylalkyl group containing from 4 to 7 carbon atoms.

6. The method of claim 4, wherein R4 represents an alkyl group containing from 1 to 6 carbon atoms, a cycloalkylalkyl group containing from 4 to 7 carbon atoms, or a group corresponding to Formula b.

7. The method of claim 4, wherein R1 represents an alkyl group containing from 3 to 6 carbon atoms or a cycloalkylalkyl group containing from 4 to 7 carbon atoms, and R4 represents an alkyl group containing from 3 to 6 carbon atoms or a cycloalkylalkyl group containing from 4 to 7 carbon atoms.

8. The method of claim 4, wherein said 3,7-diazabicyclo [3,3,1]nonane compound is a 9,9-alkylene-3,7-diazabicyclo [3.3.1]nonane compound corresponding to Formula I wherein R2 and R3 together form an alkylene chain containing from 4 to 5 carbon atoms, and R1 R4 independently of one another each denote a straight-chain or branched alkyl group of 3-4 carbon atoms or a cyclopropylmethyl group.

9. The method of claim 8, wherein said 3,7-diazabicyclo [3.3.1[nonane compound is a fumaric acid salt of said 9,9-alkylene-3,7-diazabicyclo[3.3.1]-nonane compound containing 1.5 moles of fumaric acid per mole of nonane compound.

10. The method of claim 4, wherein said 3,7-diazabicyclo [3,3,1]nonane compound is selected from the group consisting of N,N'-dicyclopropylmethyl-9, 9-tetramethylene-3,7-diazabicyclo[3,3,1]nonane, and N- isobutyl-N' isopropyl-9, 9-pentamethylen-3,7-diazabicyclo[3,3,1]nonane.

11. The method of claim 10, wherein said 3,7-diazabicyclo[3,3,1]nonane compound is a fumaric acid salt of N,N'- dicyclopropylmethyl-9, 9-tetramethylene-3,7-diazabicyclo[3,3,1] nonane or of N-isobutyl-N'-isopropyl-9, 9-pentamethylene-3,7- diazabicyclo[3,3,1]nonane containing 1.5 moles of fumaric acid per mole of nonane compound.

12. The method of claim 4, wherein said 3,7-diazabicyclo [3,3,1]nonane compound is a hydrochloride salt.

13. A method of treating an arrhythmic event in a human patient suffering therefrom, said method comprising administering to said patient by continuous infusion a single dose of an effective arrhythmia inhibiting amount of at least one 3,7-diazabicyclo [3,3,1]nonane compound or a physiologically acceptable acid addition salt thereof, in two successive phases, wherein in the first phase a first part of the continuously administered single dose is administered at a first rate over a first time period of from about 8 to about 12 minutes, and in the second phase a second part of the continuously administered single dose is administered at a second, slower rate over a second time period of from about 15 to about 25 munutes.

14. The method of claim 13, wherein said compound is administered over a first time period of from about 9 to about 11 minutes.

15. The method of claim 13, wherein said compound is administered over a first time period of from about 9.5 to about 10.5 minutes.

16. The method of claim 13, wherein said compound is administered over a second time period of from about 17 to about 23 minutes.

17. The method of claim 13, wherein said compound is administered over a second time period of from about 19 to about 21 minutes,

* * * * *